US007189200B2

(12) United States Patent
Chen

(10) Patent No.: US 7,189,200 B2
(45) Date of Patent: Mar. 13, 2007

(54) ANIMAL-USE ARTIFICIAL INSEMINATOR

(76) Inventor: Sheng-Jui Chen, No.68, Jong Luen Rd., Tzyy Guan Hsiang, Gau Shyong (TW)

( * ) Notice: Subject to any disclaimer, the term of this patent is extended or adjusted under 35 U.S.C. 154(b) by 288 days.

(21) Appl. No.: 10/962,422

(22) Filed: Oct. 13, 2004

(65) Prior Publication Data

US 2006/0079731 A1 Apr. 13, 2006

(51) Int. Cl.
*A61B 17/43* (2006.01)

(52) U.S. Cl. ........................................ 600/35; 604/264

(58) Field of Classification Search ............ 600/33–35; 604/514–520, 263–265, 271, 275; 206/363–365, 206/438–440
See application file for complete search history.

(56) References Cited

U.S. PATENT DOCUMENTS 4,453,936 A * 6/1984 Cassou ........................ 604/263
4,457,313 A * 7/1984 Alter .......................... 600/572
4,493,700 A * 1/1985 Cassou et al. ................ 600/35
2005/0107659 A1* 5/2005 Cassou ........................ 600/34

* cited by examiner

*Primary Examiner*—John P. Lacyk
(74) *Attorney, Agent, or Firm*—Rosenberg, Klein & Lee

(57) ABSTRACT

An improved animal-use artificial inseminator comprised of an insemination tube with a nozzle at its front extremity into which an insemination sheath is inserted and a connector at the rear extremity of the insemination tube having a check membrane. After the insemination tube penetrates the female animal body vagina and the front end of the nozzle is nominally at the first cervical ring of the cervix, the semen bottle insertion tube is utilized to pierce the connector check membrane at the rear extremity of the insemination tube and when the semen at the insemination tube is squeezed, semen is automatically squeezed out of the insemination sheath. The soft insemination sheath proceeds along the cervix without the occurrence of friction, the front end smoothly moving forward until it reaches the position of the womb. Contractions of the womb are utilized to articulate the insemination sheath such that the contained semen is ejaculated into the two Fallopian tubes or the womb from the slits along the two sides of the front end. At the same time, after the semen bottle is pulled out, since the connector check membrane automatically opens and closes along with the contraction of the womb, not only is the semen in the insemination sheath prevented from backflow or leakage, but air is admitted for smooth and complete squeezing into the Fallopian tubes or the womb.

5 Claims, 17 Drawing Sheets

ANIMAL-USE ARTIFICIAL INSEMINATOR

BACKGROUND OF THE INVENTION

1) Field of the Invention

The invention herein relates to an improved animal-use artificial inseminator, specifically a kind that is of a simple arrangement, easy to utilize, convenient, and enables animal semen to be rapidly and, furthermore, efficiently deposited into the two Fallopian tubes or the womb, significantly raising artificial insemination success rate and saving artificial insemination-use animal semen. Fully realizing the use of minimal amounts of insemination semen and the resulting economic benefit, the invention herein also enables safer, more hygienic, and more ergonomic artificial insemination. As such, the present invention is practical, ideal, and progressive. Furthermore, such an improved animal-use artificial inseminator is unprecedented.

2) Description of the Prior Art

Prior art animal-use artificial inseminator arrangements and operation, as indicated in FIG. 1 and FIG. 2, are typically comprised of a plastic insemination tube 10 of a certain hardness and a softer nozzle 20 installed on the front extremity of the insemination tube 10. When the artificial insemination procedure is executed, the said insemination tube 10 is inserted along the female animal body 1 vagina 11 until the nozzle 20 at the front extremity penetrates the cervix 12 position, the insertion tube 31 of the semen bottle (bag or syringe barrel) 30 containing the animal semen is inserted into the insemination tube 10 rear extremity, and since the operating personnel continuously squeezes the semen bottle (bag or syringe barrel) 30, the contained semen is ejaculated into the cervix 12 through the insemination tube 10 nozzle 20, the contraction of the womb 13 inducing the semen into the said cervix 12. Although the operation of such artificial inseminators is capable of effectively engendering animal artificial insemination, the existent shortcomings are as follows:

1. After the said insemination tube 10 penetrates the female animal body 1 vagina 11, since the nozzle 20 at the front extremity is largely proximate to the position of the cervix 12 first cervical ring 121 but the said first cervical ring 121 distance from the womb 12 still has a remaining depth, although womb 13 contraction induces the semen into the cervix 12, a large volume of semen ejaculated from the nozzle 20 initially accumulates at the position of the first cervical ring 121 and cannot immediately flow into the womb 13, the semen accumulated at the first cervical ring 121 often backflowing outside the vaginal orifice 111 and, as such, not only is there the economic shortcoming of wasted semen, at the same time, the amount of semen that flows into the womb 13 is proportionately lessened and there is a decrease in the successful insemination rate.

2. Since the said insemination tube 10 semen is directly released from the nozzle 20, when the nozzle 20 automatically penetrates the cervix 12 from the outside of the female animal body 1, the accidental admittance of contaminants from outside the body or the vagina 11 is difficult to avoid as the semen flows into the womb 13 and, as such, dangerous infection and inflammation of the vagina, cervix, and womb of the animal easily results during the artificial insemination process and, at the same time, the safety of young carried in the womb 13 is endangered.

3. To increase artificial insemination success rate and safety, the animal artificial insemination procedural operation requires specialized personnel (such as veterinarians or specialized technical personnel) and, as such, to domestic animal raisers (such pig farmers) in the animal husbandry industry, the heavy economic burden incurred and matching manpower requirements are shortcomings.

4. After the operating personnel utilizes the insemination tube 10 nozzle 20 to penetrate the female animal body 1 vagina 11 and cervix 12, besides having to place the palm on the rear extremity of the insemination tube 10, the other hand must grip and squeeze the semen bottle 30, an inefficiency shortcoming because of an obviously troublesome operation that is inconvenient, bothersome, and time consuming.

Of course, to enable animal artificial insemination that is efficient and ergonomic, there are manufacturers that currently supply accessory devices for artificial inseminators; as indicated in FIG. 3 and FIG. 4, such devices provided include an AI Buddy 40, an elastic saddle-like apparatus resembling the two front legs of an animal, wherein the rear end of an unfolding connector 50 is installed to the rear extremity of the insemination tube 10, with a locating belt 41 positioned between the AI Buddy 40 and the connector 50; as such, during the artificial insemination procedure, the operator straddles the AI Buddy 40 over the back of the female animal 1 such that the female animal feels that a male animal has mounted with its two front legs, a guide sleeve 60 is then placed at the female animal 1 vaginal orifice 111 and after the insemination tube 10 nozzle 20 penetrates the vagina 11 and reaches the cervix 12 through the guide sleeve 60, the rear extremity of the said insemination tube 10 is flexed upward and directly connected to the AI Buddy 40 locating belt 41; following the ingress of a semen bottle 30 insertion tube 31 into the connector 50, the operator only has to squeeze the semen bottle 30. In such approaches, the operation of the said prior art artificial inseminator requires the simultaneous use of both hands, one for grasping the insemination tube 10 and one for squeezing the semen bottle 30, a procedure that is troublesome and time consuming, but nevertheless an effective improvement. However, existent shortcomings that have not been improved include semen backflow that wastes semen, which is uneconomical and lowers insemination success rate; the easy inflow of contaminants from the outside of the female animal body into the vagina, cervix, and womb that endanger the health of the female animal and young carried in the womb; and the requiring of specialized personnel for operation, which is uneconomical and involves additional manpower.

SUMMARY OF THE INVENTION

The primary objective of the invention herein is to provide an improved animal-use artificial inseminator in which when an insemination sheath is inserted into the nozzle on the insemination tube and a semen bottle containing semen is squeezed at the insemination tube, semen is automatically squeezed out as the front extremity is pushed forward along the cervix without friction into the position of the womb, with the semen in the said semen bottle driven by contractions of the womb and directly ejaculated into the two Fallopian tubes or the womb via slits in the two sides of the front extremity.

Another objective of the invention herein is to provide an improved animal-use artificial inseminator in which a connector at the rear extremity of the said insemination tube has a check membrane such that after the semen bottle insertion tube injects semen into the insemination tube insemination sheath, the said check membrane automatically opens and closes with the contractions of the womb, thereby preventing the occurrence of semen backflow and leakage, while automatically admitting air to effectively increase semen flow efficiency.

DETAILED DESCRIPTION OF THE PREFERRED EMBODIMENTS

Figure 1:
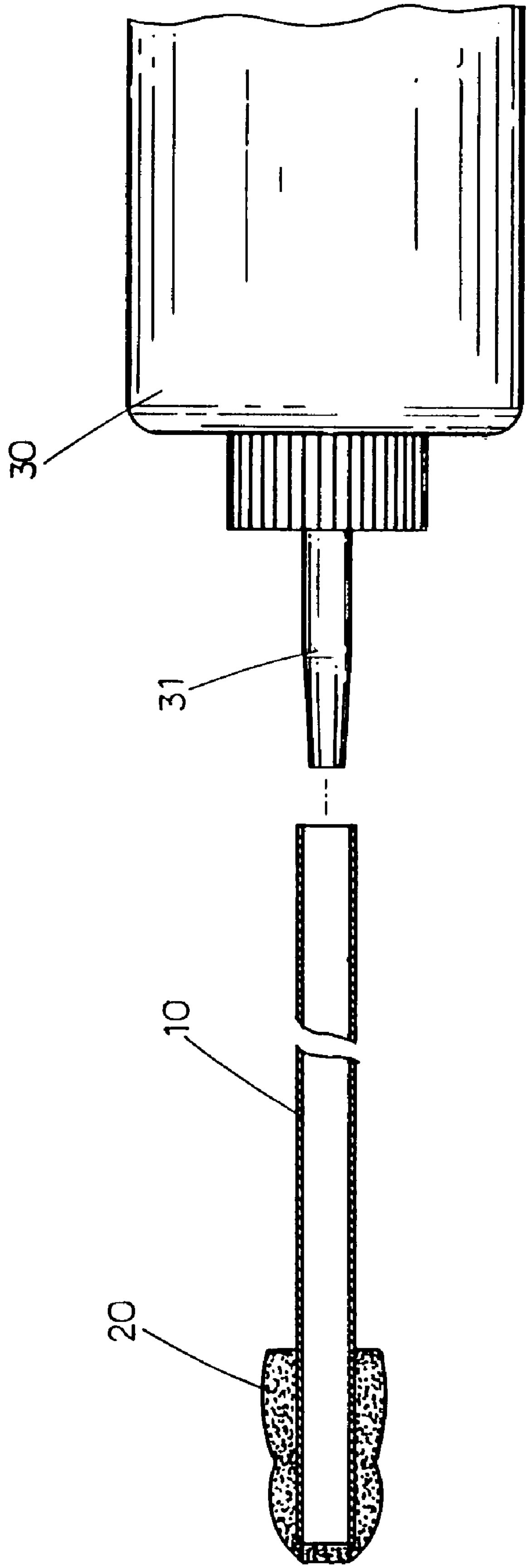
FIG.1 PRIOR ART
FIG. 1 is an orthographic drawing of the semen bottle of a prior art artificial inseminator.
Figure 2:
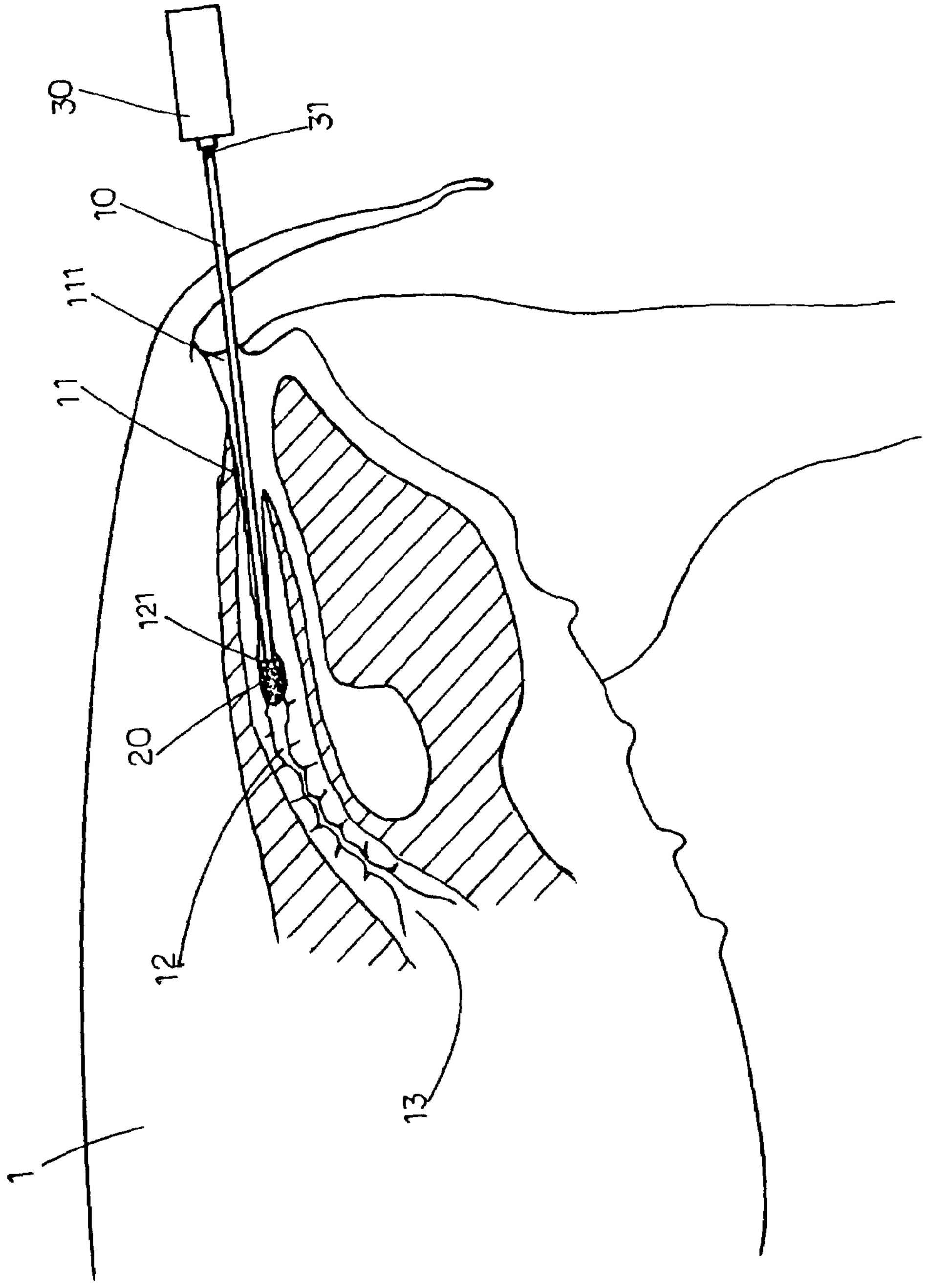
FIG.2 PRIOR ART
FIG. 2 is an orthographic drawing of the artificial inseminator in FIG. 1 penetrating the body of a female animal.
Figure 3:
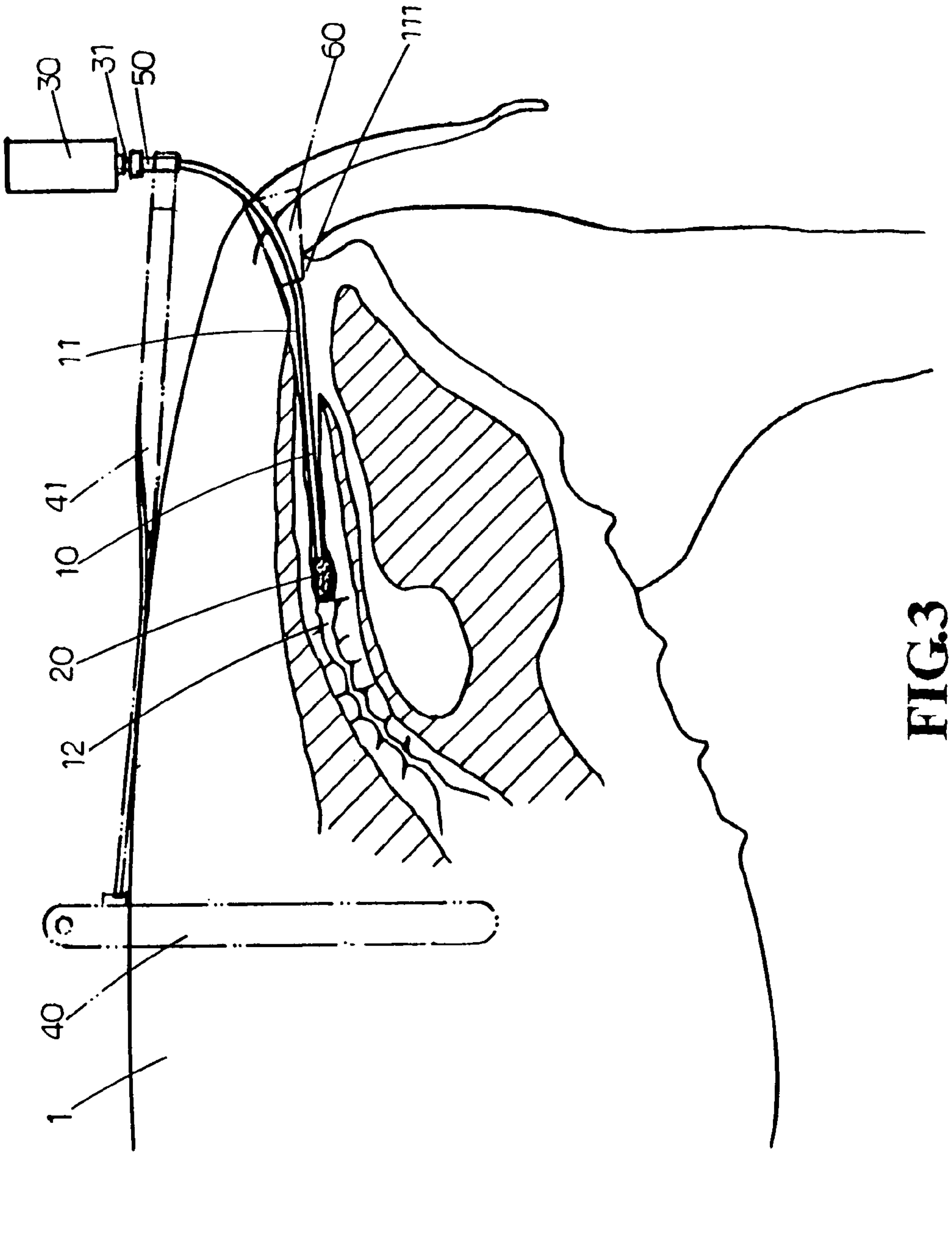
FIG.3 PRIOR ART
FIG. 3 is an orthographic drawing of the prior art artificial inseminator, equipped with a connector and an AI Buddy, penetrating the body of a female animal.
Figure 4:
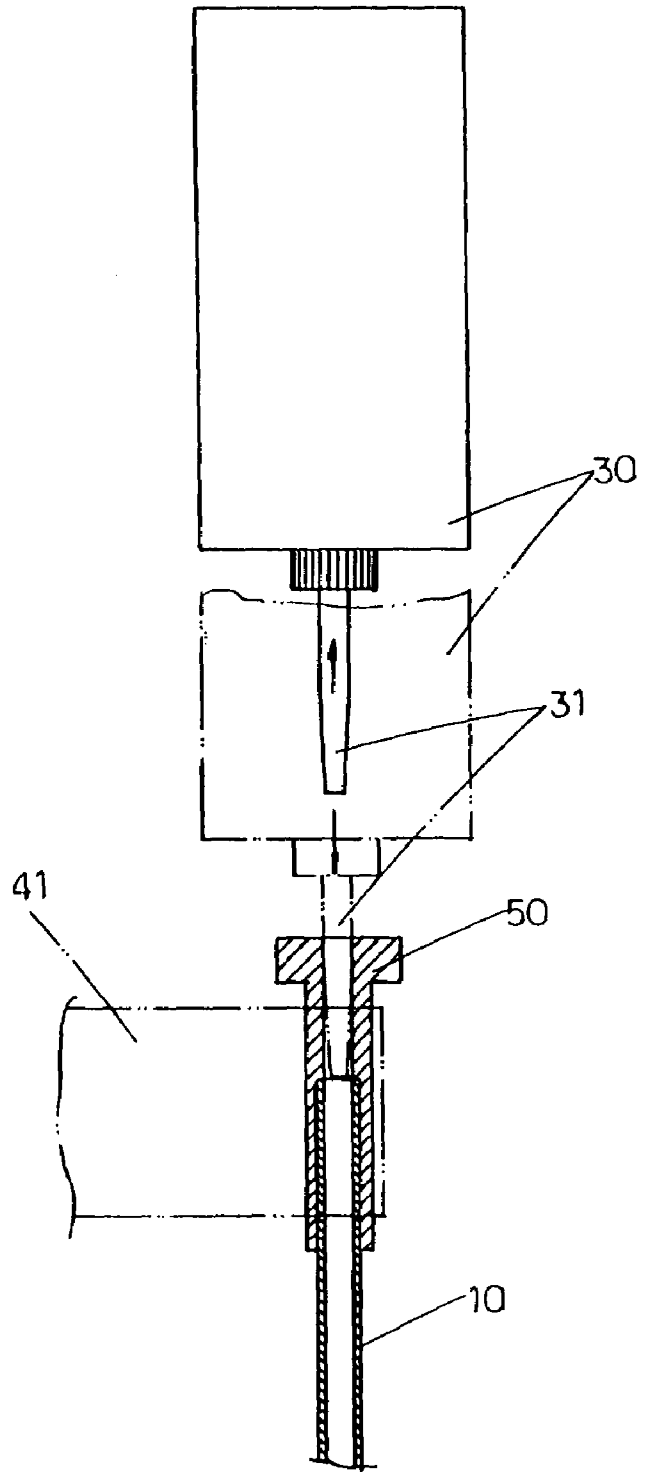
FIG.4 PRIOR ART
FIG. 4 is an orthographic drawing of the connector and the locating belt of the artificial inseminator shown in FIG. 3.

Referring to FIG. 5, FIG. 6, FIG. 7, FIG. 8, FIG. 9, FIG. 10, and FIG. 11, the improved animal-use artificial inseminator of the invention herein is comprised of an insemination tube 10 with a nozzle 20 at its front extremity into which an insemination sheath 80 is inserted, and a connector 50 at the rear extremity of the insemination tube 10 having a check membrane 51 that tightly closes a diverting passage 501, wherein:

The said insemination sheath 80 is a thin-membrane casing fabricated using a process and material similar to that involved in the production of balloons and condoms such that it possesses softness and elastic stretch characteristics; a first protruding ring 801 is unitarily formed near the rear end, the dimensions of the said first protruding ring 801 based on insertability into the nozzle 20 aperture 201; slits 802 (see FIG. 7) are juxtaposed along the two sides of the front end, with the diameter from the said front end to the first protruding ring 801 near the rear end being smaller than the inner diameter of the insemination tube 10; a second protruding ring 803 slightly larger than the first protruding ring 801 is unitarily formed at the rear end such that a flared mouth 804 results between the two protruding rings 801 and 803, and the dimensions of the flared mouth 804 are smaller than that of the nozzle 20. During the assembly and installation operation, the operator reverse inserts the front end of the insemination sheath 80 into the nozzle 20 aperture 201 at the front extremity of the insemination tube 10 to seat the first protruding ring 801 at the aperture 201 position of the nozzle 20 (see FIG. 9) and, then, utilizing the said flared mouth 804 between the said first protruding ring 801 and second protruding ring 803, the operator pushes the said flared mouth 804 back along the exterior of the nozzle 20 (see FIG. 9) such that it surrounds the entire nozzle 20 and the second protruding ring 803 tightly engages the rear end of the nozzle 20 (see FIG. 5), and since the said flared mouth 804 is smaller than the nozzle 20 and, furthermore, possesses elastic stretch characteristics, after it surrounds the nozzle 20, this ensures the expected tightness, adhesion, and sturdiness required to effectively maintain positioning.

The said check membrane 51 (see FIG. 10 and FIG. 11) disposed at the connector 50 is constructed of a rubber (or synthetic rubber) and is a thin film unitarily formed when the connector 50 is molded to close off the diverting passage 501 and consists of a slanted, downward incision to form a left and a right membrane element 511 and 512, with the said left and right membrane elements 511 and 512 having flush beveled surfaces 5110 and 5120.

Figure 12:
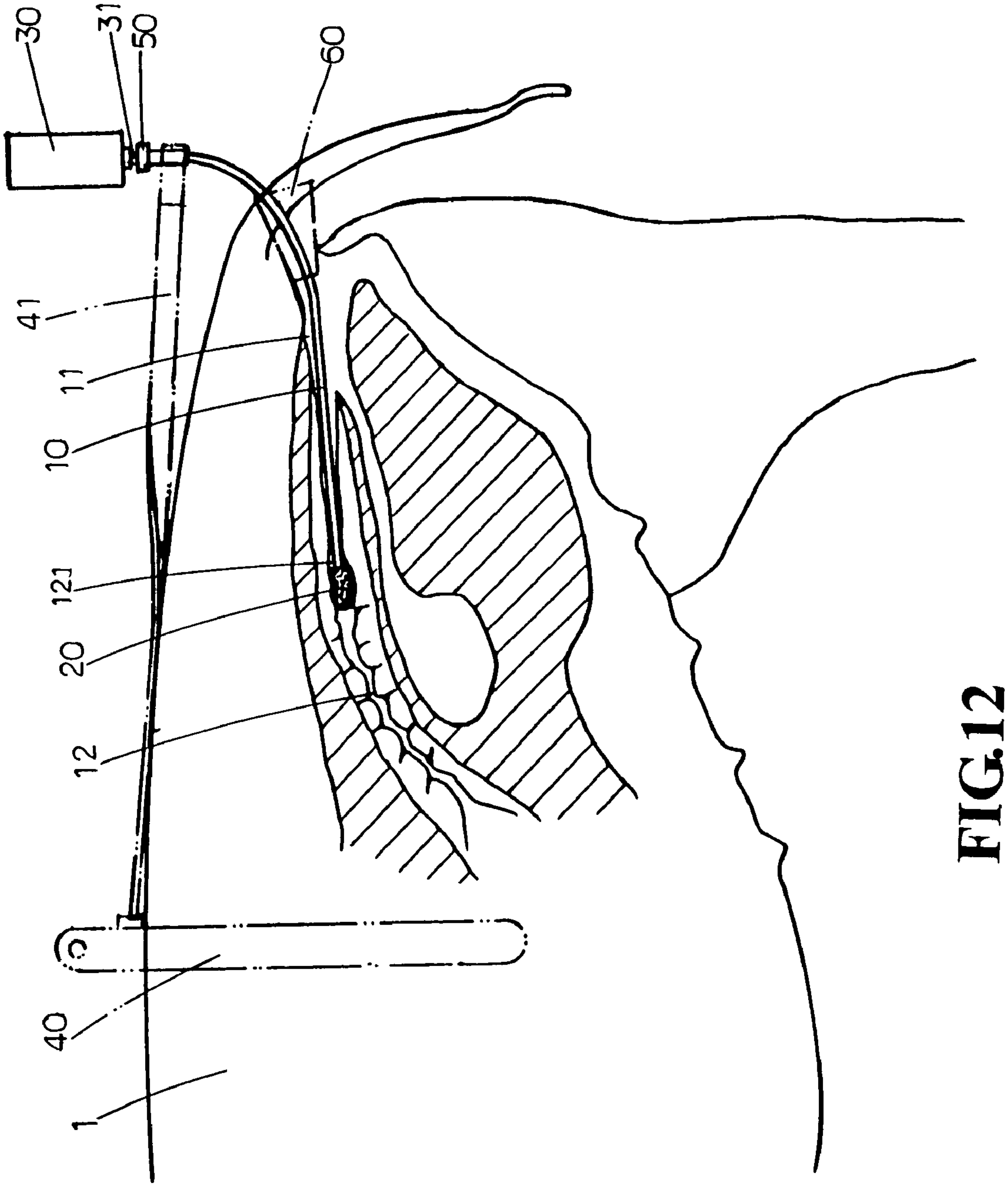
FIG. 12 is an orthographic drawing of the invention herein penetrating the body of a female animal.
Figure 13:
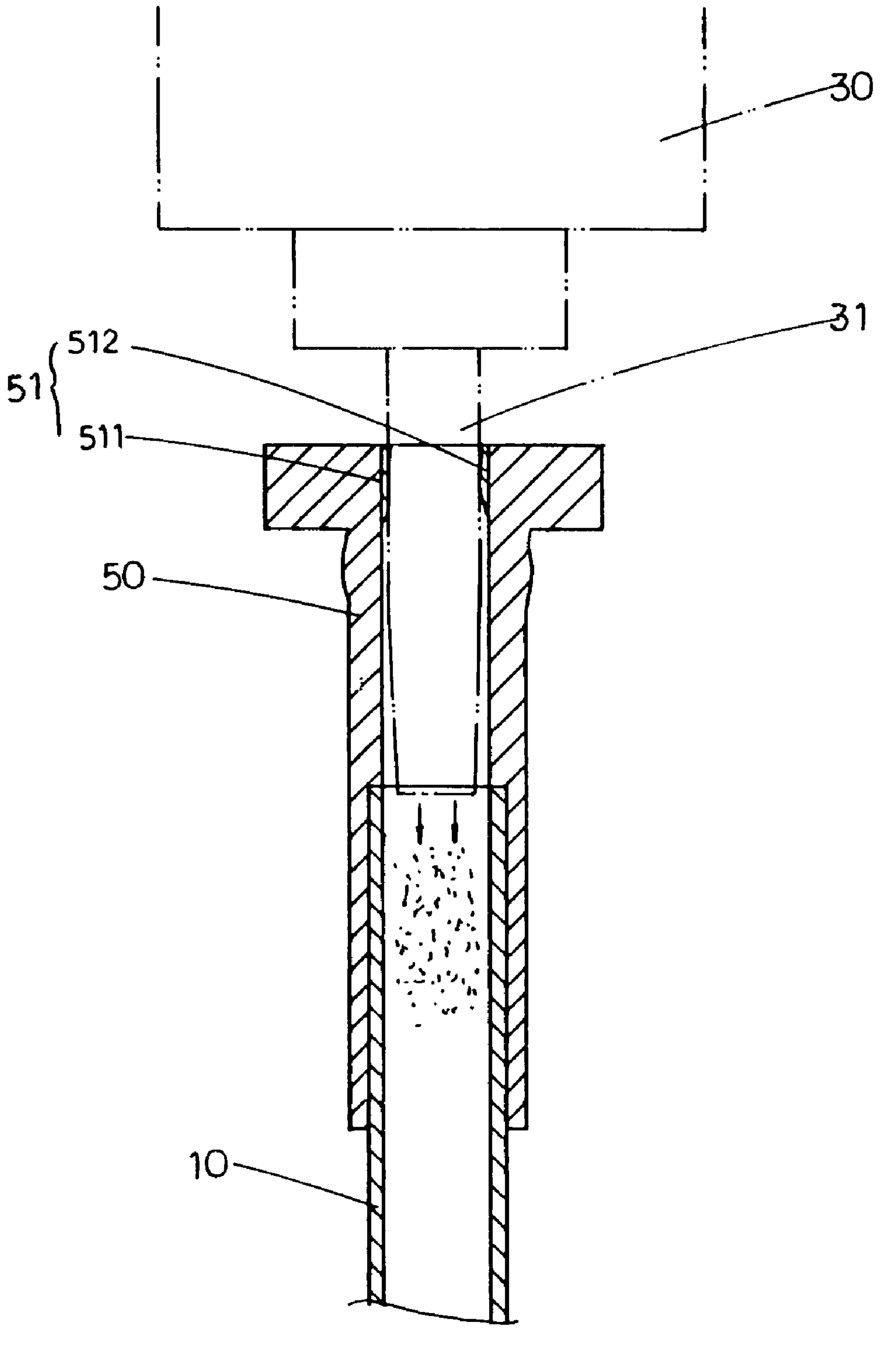
FIG. 13 is an orthographic drawing of the semen bottle insertion tube slipped into the connector of the invention herein.

Utilizing the said structure of the invention herein, referring to FIG. 12, when artificially inseminating an animal, the operator first insertionally positions the insemination sheath 80 at the insemination tube 10 nozzle 20 area according to the said method; the said insemination tube 10 is then passed through a guide sleeve 60, as per standard operating procedures, and inserted into the female animal body 1 vagina 11 until the front end of the nozzle 20 is approximately extended into the cervix 12 first cervical ring 121 position and the connector 50 at the rear extremity of the insemination tube 10 is, like the prior art, flexed upward and positioned by conjoinment to the AI Buddy 40 locating belt 41; the said semen bottle 30 insertion tube 31 is accurately slipped into the connector 50 check membrane 51 (as shown in FIG. 13); and after an appropriate volume of semen is squeezed into insemination tube 10, the rear extremity is pulled out.

Figure 5:
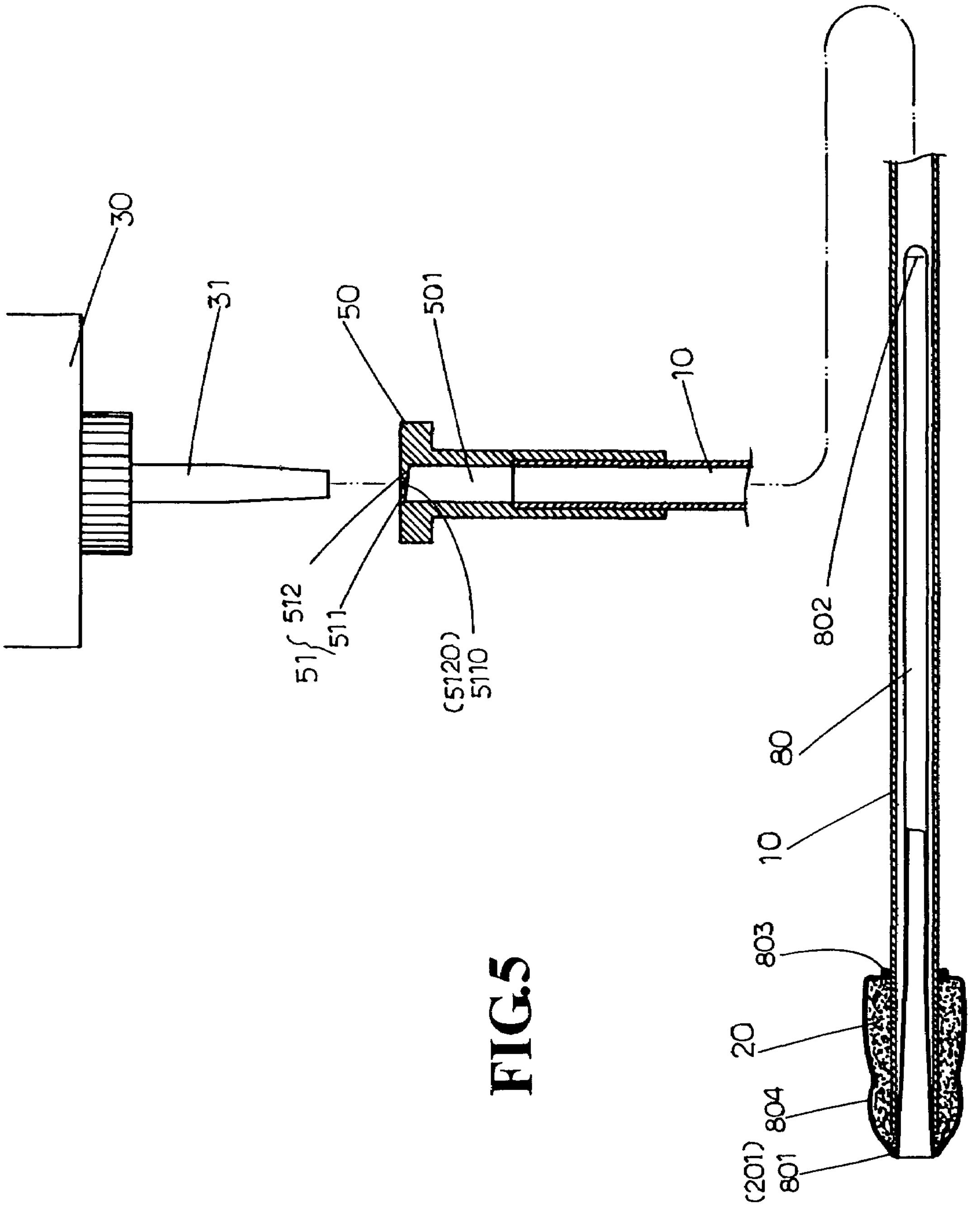
FIG. 5 is an orthographic drawing of the invention herein.
Figure 6:
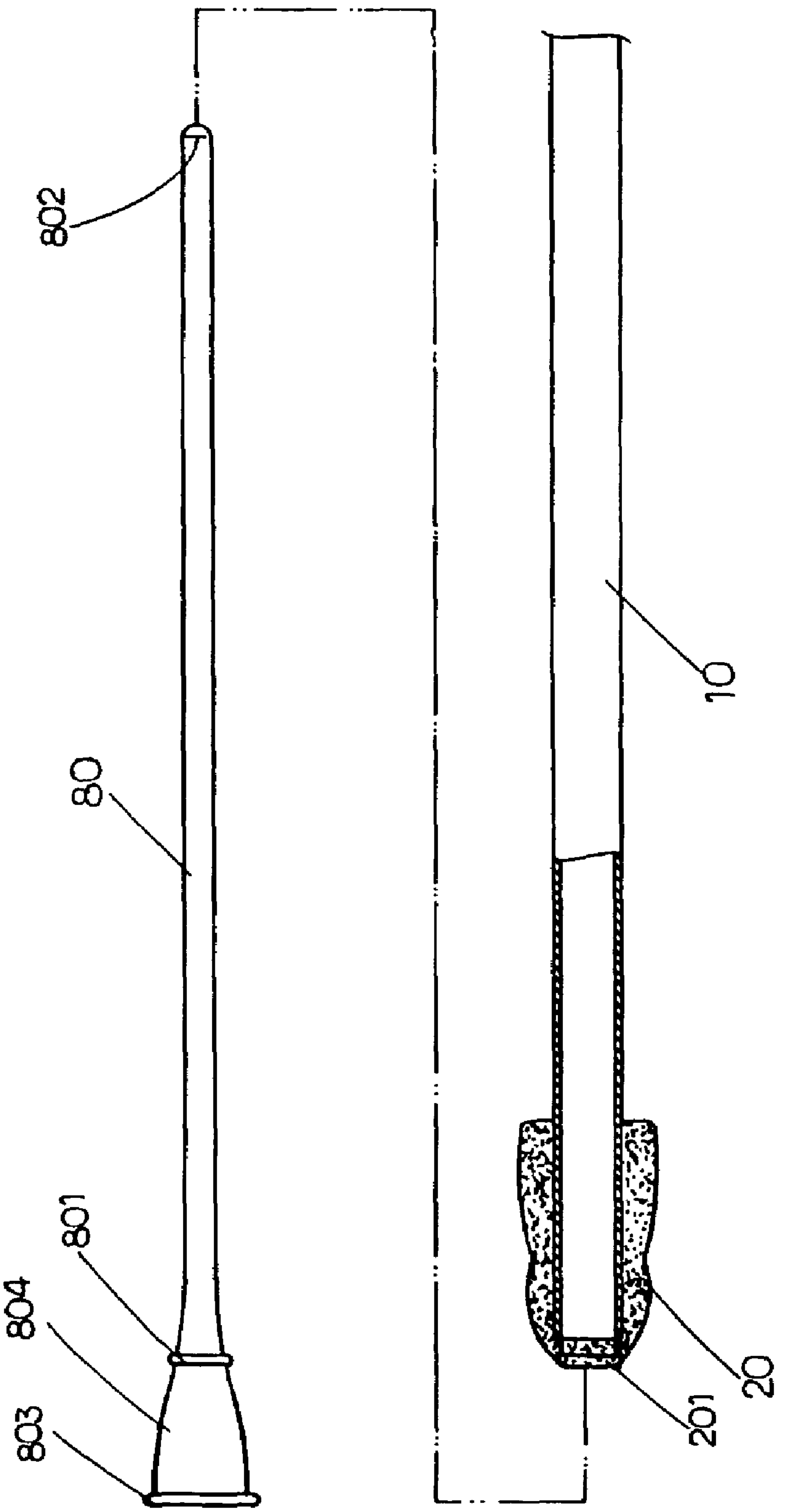
FIG. 6 is an orthographic drawing of the insemination tube and the insemination sheath of the invention herein in a separated state.
Figure 8:
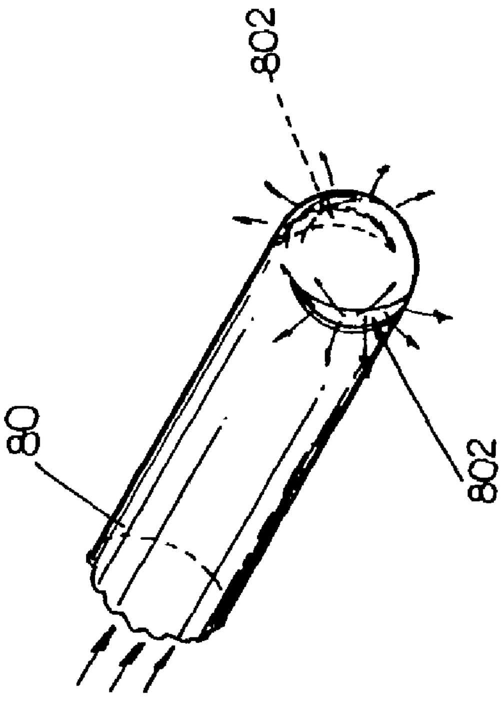
FIG. 8 is an isometric drawing of the insemination tube of the invention with the slits at the front extremity in the open state.
Figure 7:
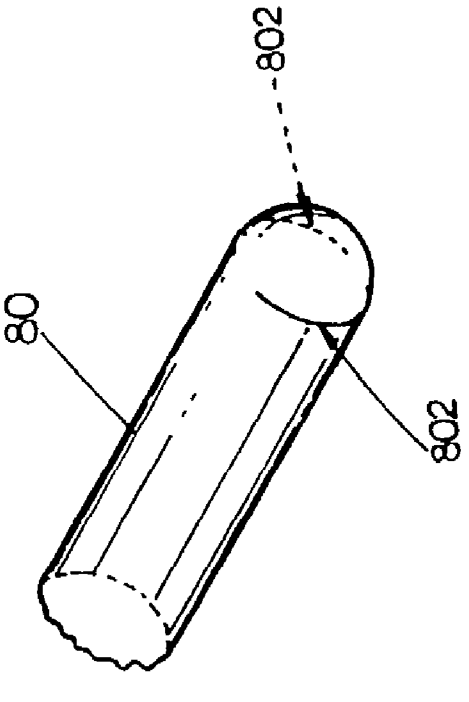
FIG. 7 is an isometric drawing of the insemination tube of the invention with the slits at the front extremity in the closed state.
Figure 9:
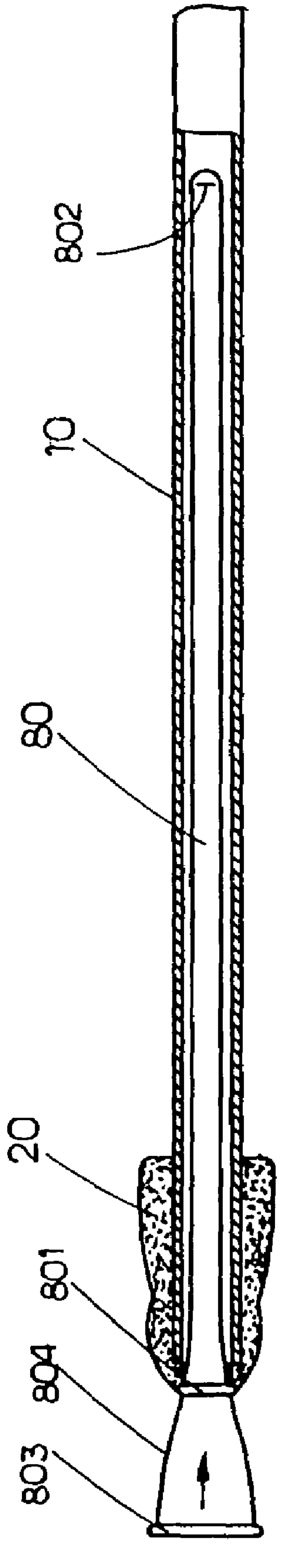
FIG. 9 is an orthographic drawing of the insemination sheath of the invention herein inserted into the insemination tube.
Figure 11:
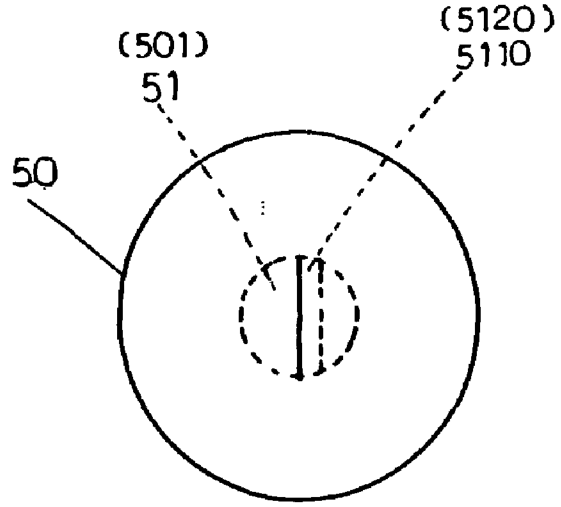
FIG. 11 is a cross-sectional drawing of the connector of the invention herein, as viewed, from above.
Figure 10:
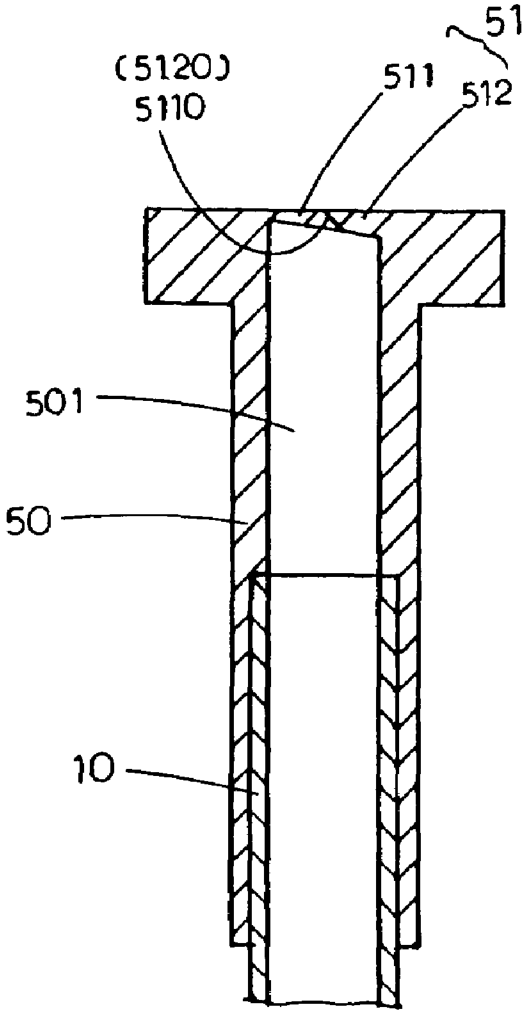
FIG. 10 is a cross-sectional drawing of the connector of the invention herein, as viewed from the front.
Figure 14:
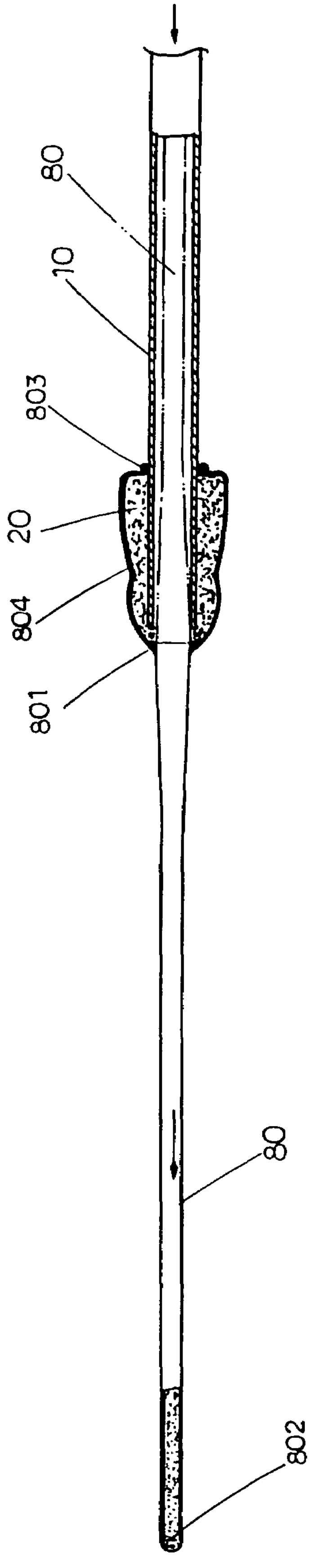
FIG. 14 is an orthographic drawing of the insemination tube of the invention herein in the distended state.
Figure 15:
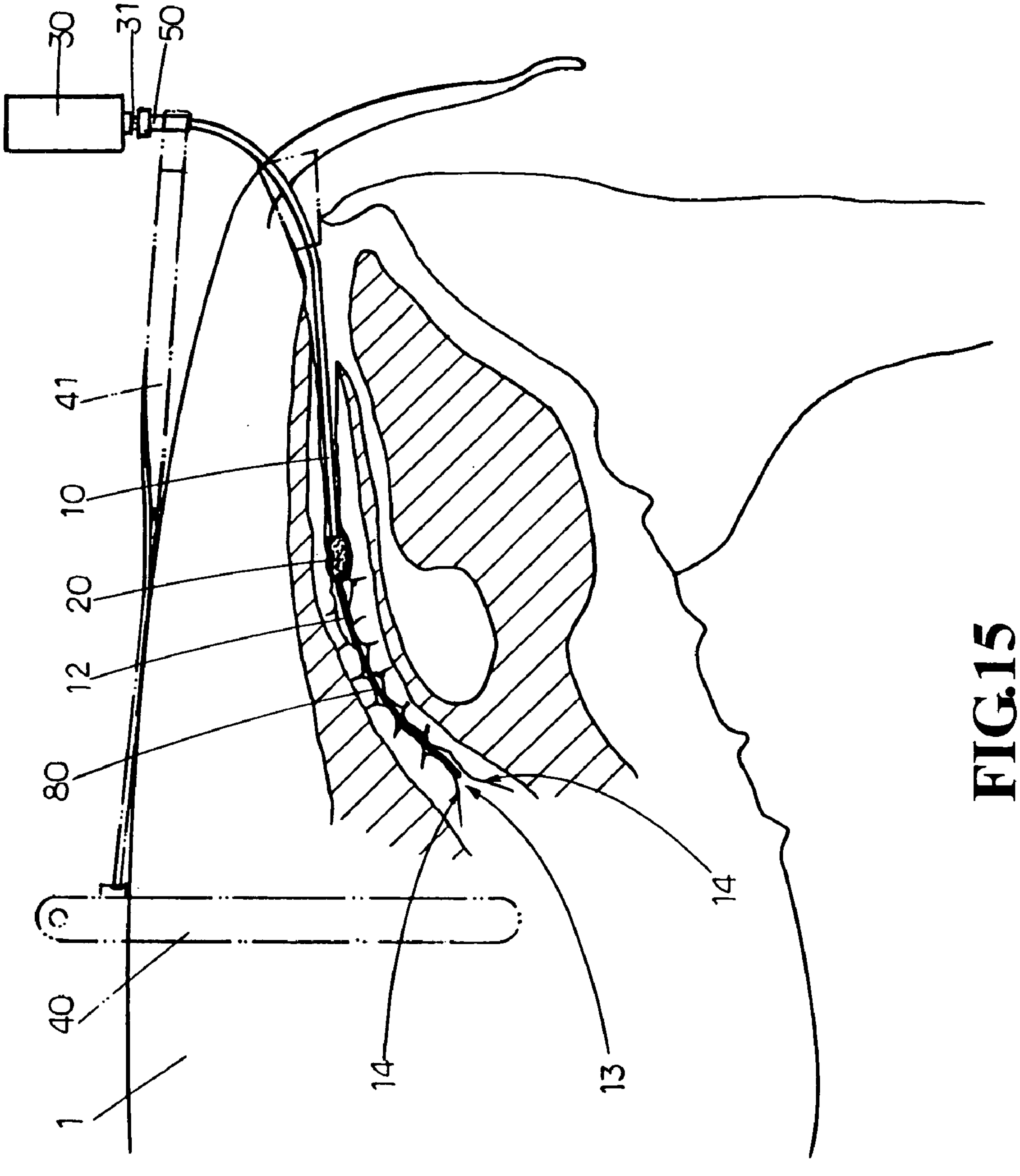
FIG. 15 is an orthographic drawing of the invention herein penetrating the female animal body until the insemination sheath opens.

When the semen in the said semen bottle 30 is squeezed into the insemination tube 10, as indicated in FIG. 5 and FIG. 14, the insemination sheath 80 ensconced within the insemination tube 10 is subjected to pressure, and automatically squeezed out in the opposite direction to distend from the inside of the front extremity and, furthermore, as the semen is squeezed in, as indicated in FIG. 15, the said insemination sheath 80 distending towards the front is pushed forward into the female animal body 1 cervix 12 such that the front extremity is directly extended to the position of the two Fallopian tubes 14 or the womb 13. As such, since the said insemination sheath 80 has soft characteristics, when subjected to squeeze pressure and distended towards the front, it flexes along the cervix 12 without the occurrence of friction, smoothly expanding forward into the narrow tubes such that not only is the front extremity efficiently pushed to the deep area of the cervix 12 at the position of the two Fallopian tubes 14 or the womb 13, but is accomplished without injury or inflicting pain to the fragile tissue of the cervix 12, thereby achieving artificial insemination that is even more ergonomic and safe.

Since the said second protruding ring 803 at the rear end of the said insemination sheath 80 is elastically engaged at the rear end of the nozzle 20, when the insemination sheath 80 is subjected to pressure and distends towards the front in the direction of the cervix 12 and womb 13 area, dislodging due to loosening does not occur.

Figure 16:
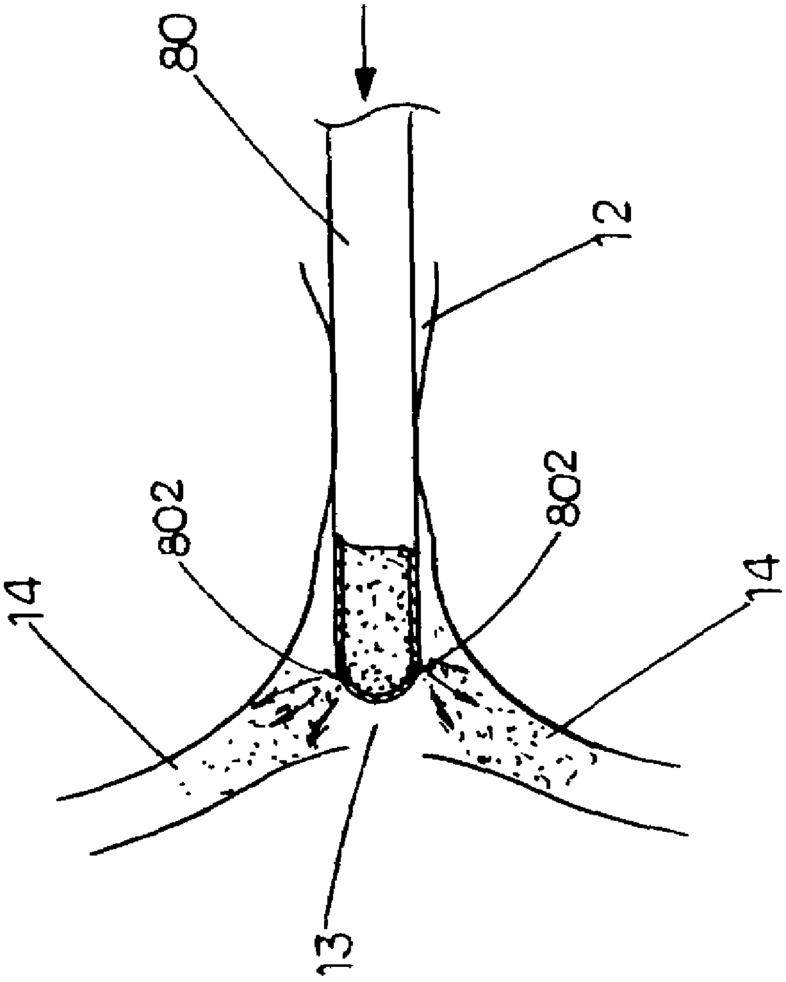
FIG. 16 is an orthographic drawing of the insemination sheath of the invention herein with the front end opened at the womb position of the female animal body.

Furthermore, since the slits 802 (see FIG. 7) are juxtaposed along the two sides of the said insemination sheath 80, after the front end distends to the position of the two Fallopian tubes 14 or the womb 13, due to the pressure of the injected semen, the said two slits 802 are automatically forced open (see FIG. 8), enabling the contained semen to be rapidly ejaculated into the two Fallopian tubes 14 or the womb 13 (see FIG. 16).

Figure 18:
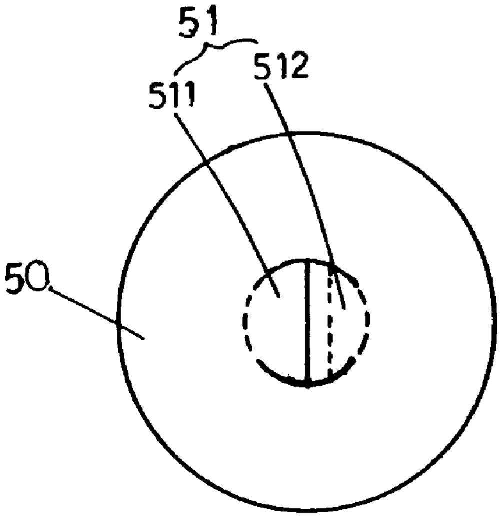
FIG. 18 is an orthographic drawing of FIG. 17, as viewed from above.
Figure 17:
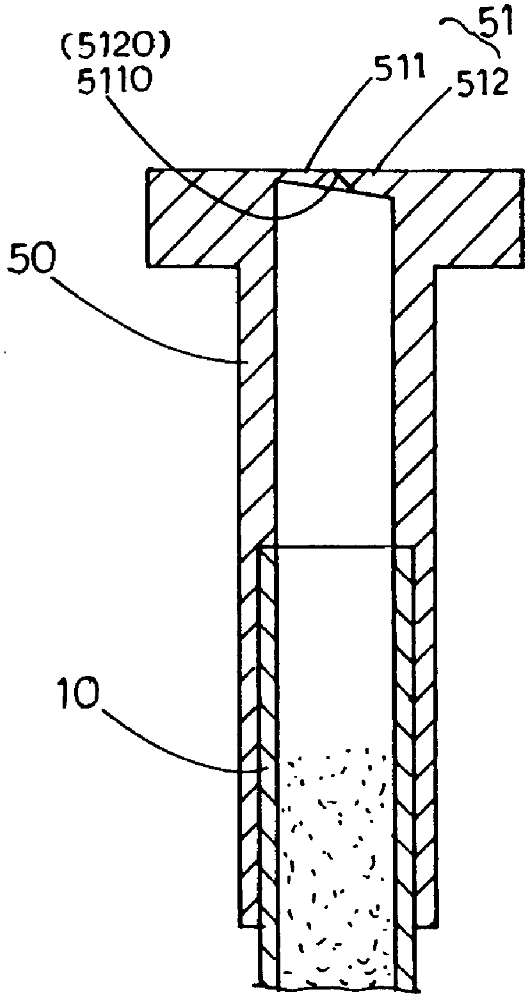
FIG. 17 is an orthographic drawing of the semen bottle in FIG. 13 connector in the closed state after it is pulled out.

Furthermore, an appropriate volume of semen is injected from the semen bottle 30 into the insemination tube 10 until the insemination sheath 80 is fully distended, and after the semen bottle 30 is pulled out from the connector 50 area, as indicated in FIG. 13, FIG. 17, and FIG. 18, the left and right membrane elements 511 and 512 originally pierced apart by the semen bottle 30 insertion tube 31 are automatically restored upward by inherent elastic tension, their respective beveled surfaces 5110 and 5120 each stacked in a sealed closure such that semen inside the insemination tube 10 cannot flow back and leak. Furthermore, since the said insemination sheath 80 is directly extended to the cervix 12 until the front end is situated at the area of the two Fallopian tubes 14 or the womb 13, utilizing the contractive action of the womb 13 against the insemination sheath 80 containing the semen causes the automatic opening and closing of the slits 802 along the two sides of the front end, and when open, the semen is automatically ejaculated into the two Fallopian tubes 14 or the womb 13 in a highly efficient artificial insemination operation.

Figure 19:
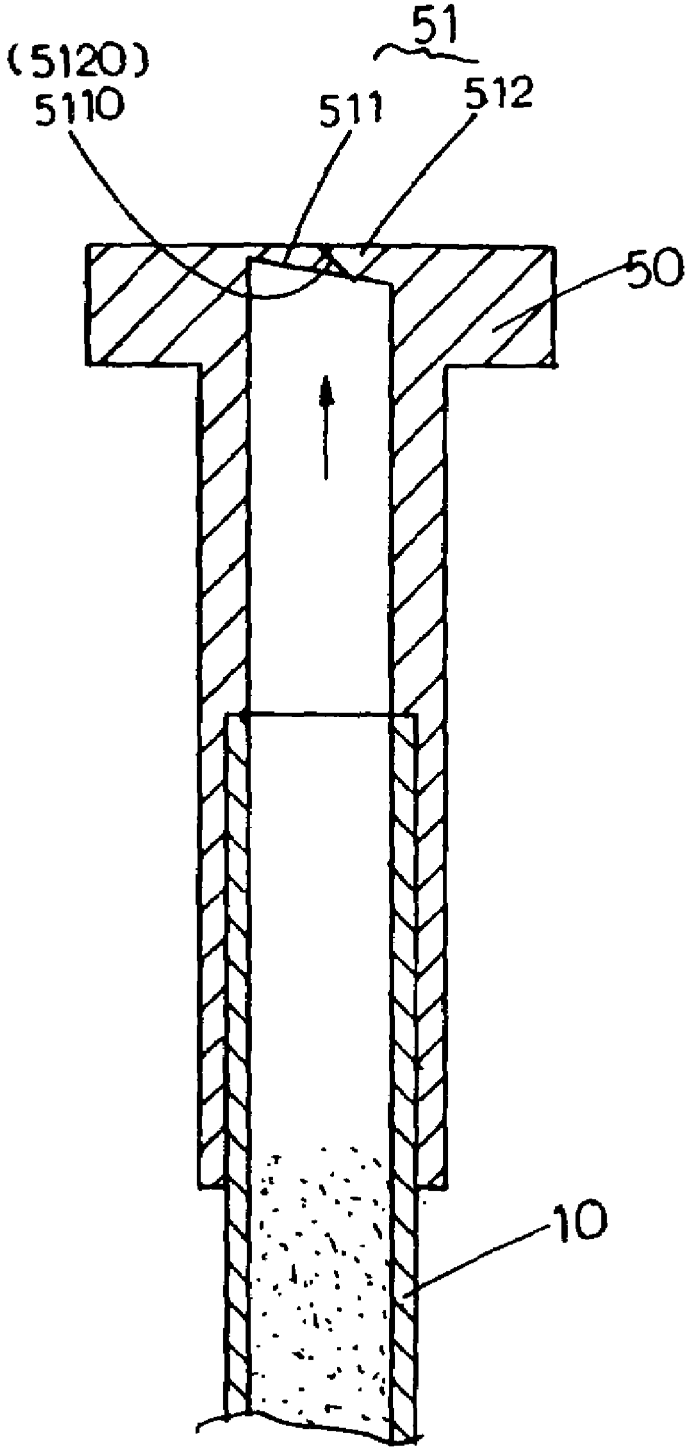
FIG. 19 is an orthographic drawing of the connector of the invention herein contracting with the womb into the closed state.
Figure 20:
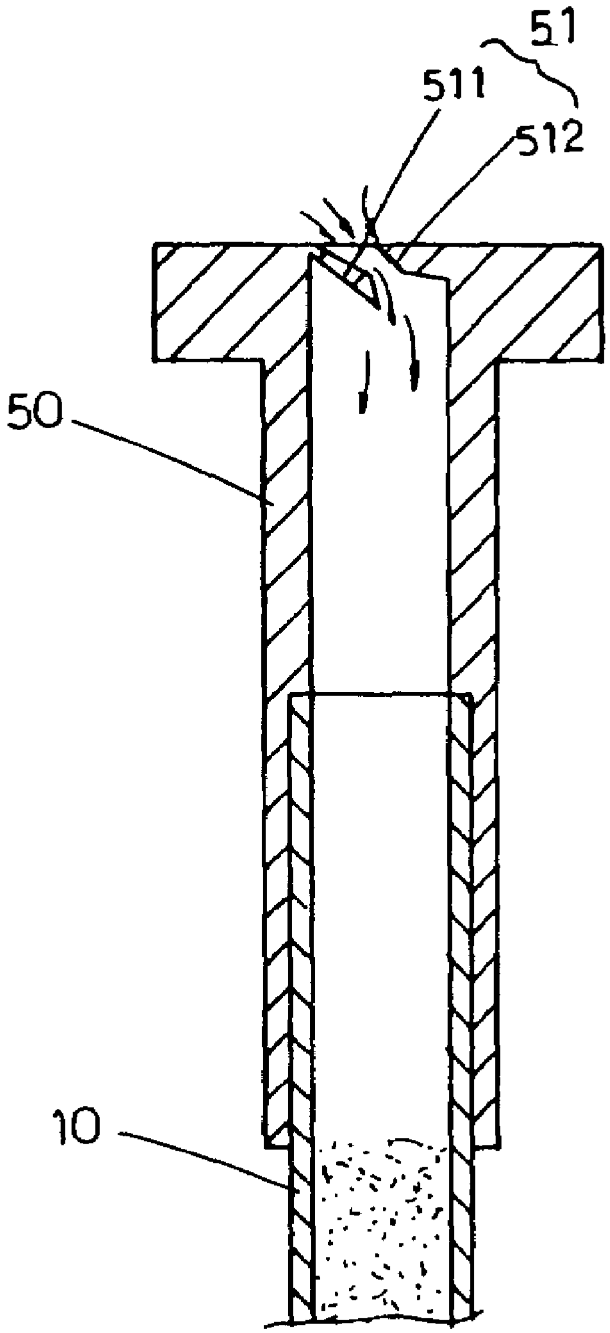
FIG. 20 is an orthographic drawing of the connector of the invention herein contracting with the womb into the open state.

Of course, when the contractional pressure of the womb 13 squeezes open the two slits 802 at the front end of the insemination sheath 80 for semen ejaculation, they are similarly subjected to the pressure of the check membrane 51, and in addition to having the left and right membrane element 511 and 512 beveled surfaces 5110 and 5120 stacked in a sealed closure to prevent semen backflow and leakage (see FIG. 19), since the said left and right membrane element 511 and 512 are of thin film construction, each time the womb 13 contracts and causes semen in the insemination sheath 80 to flow forward, as indicated in FIG. 20, the check membrane 51 automatically opens downward vertically to admit air, enabling the semen inside the insemination tube 10 insemination sheath 80 to flow forward even more smoothly such that the semen is ejaculated at an even higher efficiency into the two Fallopian tubes 14 or the womb 13.

Since the two slits 802 at the front end of the insemination sheath 80 remain in a sealed state when not subjected to squeeze pressure, even if the said semen injecting insemination tube 10 and the insemination sheath 80 are in the distended stage, the said slits 802 still maintain closure until the insemination sheath 80 is completely extended to cervix 12 such that when the front end reaches the position of the two Fallopian tubes 14 or the womb 13, they open to release the semen due to squeeze pressure, enabling semen utilization with optimum efficiency.

When the said insemination sheath 80 is fabricated, a layer of lubricating agent is applied over its inner and outer surfaces such that not only is the insertion into the insemination tube 10 and surrounding nozzle 20 even easier and more convenient, the forward distention at the cervix 12 is also smoother and faster due to the lubrication.

During fabrication, the flared mouth 804 between the first protruding ring 801 at the rear end and the second protruding ring 803 of the said insemination sheath 80 can be initially rolled inward, enabling its shape to become circular like a condom such that when assembled to the nozzle 20, the operator only has to push it easily towards the rear end of the nozzle for rapid and, furthermore, convenient fitting, surrounding, and positioning.

In other words, utilizing the said structure of the invention herein at minimum affords the following advantages:

1. Since the semen is directly released when the front end of the insemination sheath 80 extends to the area of the two Fallopian tubes 14 or the womb 13, the artificial insemination success rate is not only significantly higher, at the same time, the said prior art semen phenomenon of backflow and blockage at the cervix 12 is effectively improved and completely eliminated.

2. Since the semen is directly released when the front end of the insemination sheath 80 extends to the position of the two Fallopian tubes 14 or the womb 13, female animal body 1 or vagina 11 area contaminants cannot enter the womb 13 with the semen and, as such, the present invention effectively improves the said prior art artificial insemination process which results in dangerous bacterial infection of the female animal body 1 or vagina 11 due to contaminant inflow.

3. Since the semen is delivered directly to the position of the two Fallopian tubes 14 or the womb 13 by the insemination sheath 80, and neither backflow or leakage over the vaginal orifice or blockage at the womb 13 occurs, in addition to raising artificial insemination success rate, said utilized semen can be directly decreased which in turn lessens the quantity of male animals needed, thereby enabling the use of minimal amounts of insemination semen and increasing economic benefit.

4. Since the semen is directly released from the front end of the insemination sheath 80 extended within the position of the two Fallopian tubes 14 or the womb 13 and is not released from the nozzle 20 aperture 201 onto the cervix 12, the nozzle 20 at the front extremity of the said insemination tube 10 is inserted at the womb 13 position of the female animal body 1 without requiring extreme precision or excessive penetration, and given the operational simplicity, personnel executing the artificial insemination procedure do not have to be fully professional individuals (such as veterinarians or specialized technical personnel), truly ensuring full manpower utilization convenience and economy; and, of course, since the said nozzle 20 does not have to excessively penetrate the cervix 12 and the said insemination sheath 80 can be lubricated for extending at the cervix 12, no injury or inflicting of pain occurs at the fragile tissue of the cervix 12, thereby enabling artificial insemination to be even more ergonomic and safe.

The invention claimed is:

1. An animal-use artificial inseminator comprising:

an insemination tube, a nozzle, an insemination sheath, and a connector; wherein, said nozzle is installed at a front extremity of said insemination tube and said connector is installed at a rear extremity of said insemination tube, said insemination sheath having a front end inserted into an aperture of said nozzle at the front extremity of said insemination tube, a first protruding ring is unitarily formed near a rear end of the insemination sheath, said first protruding ring is seated at said aperture of said nozzle; slits are juxtaposed along two sides of the front end of the insemination sheath, with a diameter from said front end to said first protruding ring near the rear end thereof being smaller than an inner diameter of said insemination tube; a second protruding ring slightly larger than said first protruding ring is unitarily formed at the rear end of the insemination sheath such that a flared mouth results between said first and second protruding rings, and dimensions of said flared mouth are smaller than that of said nozzle; and said flared mouth is sleeved back along the exterior of the said nozzle until said second protruding ring tightly engages a rear end surface of said nozzle; said connector has a check membrane that closes a diverting passage, said check membrane consisting of an up and down, slanted incision forming a left and a right membrane element, with said left and right membrane elements having opposing, stacked beveled surfaces that are held flush by elastic pressure.

2. The animal-use artificial inseminator as defined in claim 1, wherein said insemination sheath is a thin-membrane casing fabricated of a soft, elastic, and stretchable material.

3. The animal-use artificial inseminator as defined in claim 1, wherein said flared mouth at the rear end of said insemination sheath is smaller than said nozzle.

4. The animal-use artificial inseminator as defined in claim 1, wherein said insemination sheath has a layer of lubricating agent applied over inner and outer surfaces thereof.

5. The animal-use artificial inseminator as defined in claim 1 or claim 3, wherein said flared mouth at the rear end of said insemination sheath is initially rolled inward to assume a circular state.

* * * * *